US00PP10129P

United States Patent [19]

Stravers

[11] Patent Number: Plant 10,129

[45] Date of Patent: Nov. 25, 1997

[54] GERBERA PLANT NAMED 'TERFLORIN'

[75] Inventor: Lambertus Johannes Maria Stravers, Kudelstaart, Netherlands

[73] Assignee: Terra Nigra Holding B.V., De Kwakel, Netherlands

[21] Appl. No.: 566,579

[22] Filed: Nov. 28, 1995

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,253 6/1990 Segers ..... Plt./68.1

P.P. 7,466 3/1991 Segers ..... Plt./68.1

P.P. 8,589 2/1994 Stravers ..... Plt./68.1

*Primary Examiner*—Howard J. Locker

[57] ABSTRACT

A new and distinct cultivar of Gerbera plant named 'Terflorin', as illustrated and described, characterized by its single type, distinct orange ray florets which are a solid orange color throughout, a very distinctive greyed-purple disc before flowering of disc florets, orange male and female mature disc florets, the outermost florets which display light yellow stigmas and the middle florets showing light yellow anthers, orange perianth lobe color and 110 mm overall flower diameter.

1 Drawing Sheet

BACKGROUND OF THE INVENTION

The present invention comprises a new and distinct cultivar of *Gerbera jamesonii*, referred to by the cultivar name 'Terflorin'.

'Terflorin' was originated from a hybridization program in De Kwakel, The Netherlands in 1992. The female parent was 'Terfacci' and the male parent was 'Fuego'. The female parent 'Terfacci' is pink and single and has a green center. Of the male parent 'Fuego' no description is available. 'Terfacci' has been available outside Terra Nigra and is the subject of U.S. Plant Pat. No. 7,848. The new cultivar was selected by me from the progeny of the stated parentage on or about September 1992. The first asexual reproduction of 'Terflorin' was accomplished when vegetative cuttings were taken on January 1993 in De Kwakel. The new cultivar is presently being propagated by cuttings and tissue culture. Horticultural examination of selected units initiated May 1995 has demonstrated that the combination of characteristics as herein disclosed for 'Terflorin' are firmly fixed and are retained through successive generations of asexual reproduction.

'Terflorin' has not been observed under all possible environmental conditions. The phenotype may vary significantly with variations in environment such as temperature, light intensity and day length. The following observations, measurements and comparisons describe plants grown in De Kwakel, The Netherlands, under greenhouse conditions which closely approximate those generally used in commercial practice.

The following traits have been repeatedly observed and are determined to be basic characteristics of 'Terflorin', which in combination distinguish this Gerbera from its parents and all other varieties of which I am aware:

1. Type: Single.
2. Color of ray floret: Orange.
3. Color of disc before flowering of disc florets: RHS187A.
4. Color of perianth lobe: Orange.
5. Diameter of flower head: 100–110 mm.

Of the many commercial cultivars known to me, there is no cultivar similar in comparison to 'Terflorin'.

BRIEF DESCRIPTION OF THE FIGURE OF THE DRAWING

The accompanying photographic drawing shows typical inflorescence characteristics with the colors being as nearly true as possible in illustrations of this type. In the following description, color references are made to The Royal Horticultural Society Color Chart (RHS). The color values were determined at 16:00 p.m. on 22 Sep. 1992 under natural light at De Kwakel.

BOTANICAL DESCRIPTION OF THE PLANT

Botanical: *Gerbera jamesonii* cv. Terflorin.

Inflorescence

A. Capitulum:
- *Form.*—Incurving funnel-shaped.
- *Type.*—Single.
- *Diameter across face.*—100–110 mm.

B. Corolla of ray florets:
- *Color (general tonality from a distance of 3 meters).*—Orange.
- *Color (topside).*—RHS 33A.
- *Color (bottom side).*—RHS 22C.

C. Corolla of disc florets:
- *Color (mature).*—Orange.
- *Color (immature).*RHS 170B.

D. Reproductive organs:
- *Stigma.*—Light yellow RHS 11C.
- *Anthers.*—Light yellow RHS 13B.
- *Pappus.*—Purple RHS 187B.

Plant A. General appearance:

*Height.*—40 cm measured excluded any flowers.

B. Foliage:
- *Color (abaxial).*—RHS 137C.
- *Color (adaxial).*—RHS 139A.
- *Shape.*—The angle of apex: acute. The shape of apex: pointed. The margin of lobes: crenate.

C. Disease resistance: No special disease resistance.

Other Characteristics

The following traits have been repeatedly observed and are determined to be basic characteristics of 'Terflorin', which in combination distinguish this Gerbera as a new and distinct cultivar.

Leaf blade:

*Length.*—Medium (approx. 45 cm).

*Width.*—Medium (approx. 18 cm).

*Thickness.*—Medium.

*Blistering.*—Medium.

*Pubescence.*—On upper side (midrib excluded): sparse.

*Depth of cuts or incisions in leaf.*—Basal part: deep. Central part: shallow. Distal part: very shallow.

*Color.*—Upper side of the leaf blade: dark green (RHS 139A). Bottom side of the leaf blade: RHS 137C.

*Glossiness on upper side.*—Medium.

*Angle of apex.*—Acute.

*Shape of apex.*—Pointed.

*Margin of lobes.*—Crenate.

*Extensions of margin.*—Medium.

*Petiole length.*—Medium (approx. 12 cm).

*Petiole coloration.*—RHS 145B.

*Petiole anthocyanin coloration.*—Medium.

Peduncle:

*Length.*—Medium (60–65 cm).

*Cross section.*—Round.

*Tendency to fasciation.*—Absent.

*Thickness.*—Medium.

*Strength.*—Medium.

*Pubescence.*—Medium.

*Color.*—Medium green RHS 143C.

*Anthocyanin coloration.*—At base: Medium. At top: absent.

*Involucral bracts.*—Absent.

Flower head:

*Type.*—Single.

*Diameter.*—Medium (approx 100–110 mm).

*Shape.*—Incurving funnel-shaped.

*Involucre.*—Height from point of attachment of involucre to top of flower head: medium (approx. 28 mm). Height: medium (approx. 20 mm). Diameter: medium (approx. 37 mm). Number of bracts: medium (approx. 45). Longitudinal axis of inner rows: reflexing. Anthocyanin: present. Pubescence: medium.

*Ray florets.*—Number: medium (52). Shape: narrow elliptic. Longitudinal axis outer row: incurring. Longitudinal axis inner row: incurring.

*Outer ray floret.*—Cross section: convex. Length: medium (approx. 45 mm). Width: narrow to medium (approx. 7–8 mm). Longitudinal folding: medium. Angle of apex: acute. Shape of apex: pointed. Incisions of apex: zero to one. Depth of incision: very shallow. Length of free petals: short. Color distribution on inner side: uniform. Edge of different color: absent. Striation: absent. Claw spot: present.

Disc florets:

*Diameter.*—Medium (approx. 32 mm).

*Main color perianth lobes.*—Female flowers: orange. Male flowers: orange.

Reproductive parts:

*Style.*—Main color distal part: red-orange between RHS 31B and 31C.

*Stigma.*—Main color: light yellow RHS 11C.

*Anthers.*—Main color: light yellow RHS 13B. Color of top relative to other parts is identical. Longitudinal stripes are absent. Intensity of anthocyanin coloration is absent or very weak.

*Pappus.*—Main color: purple RHS 61A. Color of top relative to other parts is identical. Level of top relative to closed disc florets: just above.

*Fertility*—Fertility as well as the seed setting is good.

I claim:

1. A new and distinct cultivar of Gerbera plant named 'Terflorin' substantially as herein shown and described, characterized particularly as to novelty by its characteristics enumerated above.

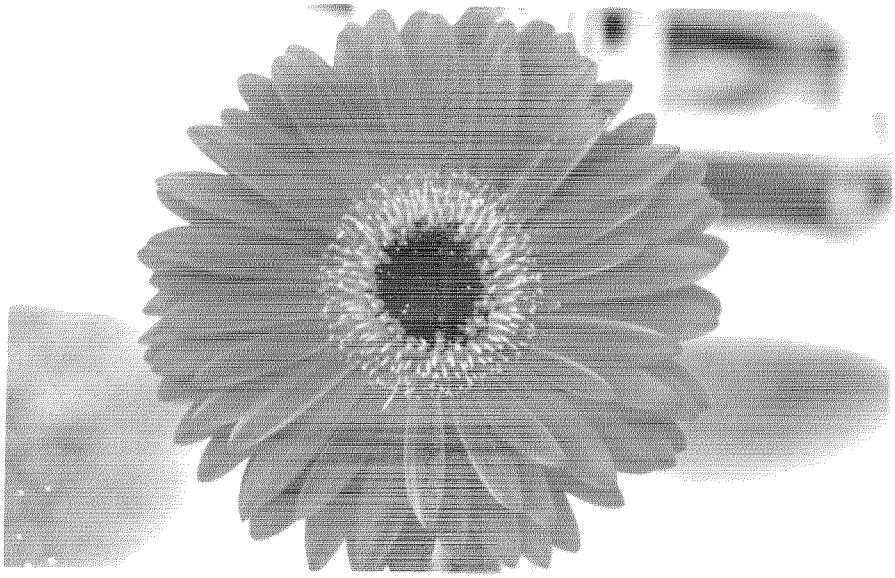

* * * * *